United States Patent [19]

Bochinski

[11] 4,025,311

[45] May 24, 1977

[54] PROGRAMMED FLUID SAMPLING AND ANALYSIS APPARATUS

[76] Inventor: Julius H. Bochinski, 26 Redding Ridge Drive, Gaithersburg, Md. 20760

[22] Filed: Jan. 9, 1976

[21] Appl. No.: 647,776

[52] U.S. Cl. .............................. 23/253 R; 222/373; 23/253 A
[51] Int. Cl.² .................... B67D 5/40; G01N 31/00
[58] Field of Search ......... 23/253 R, 253 A, 230 A, 23/259; 222/373

[56] References Cited

UNITED STATES PATENTS

| | | | |
|---|---|---|---|
| 2,063,140 | 12/1936 | Allison | 23/230 A X |
| 3,081,158 | 3/1963 | Winter | 23/253 R |
| 3,129,162 | 4/1964 | Jones | 222/373 X |
| 3,422,271 | 1/1969 | Fuhrmann | 23/253 R X |
| 3,471,262 | 10/1969 | Hrdina | 23/253 R X |
| 3,627,494 | 12/1971 | Fahnrich | 23/259 |
| 3,654,113 | 4/1972 | Bochinski | 23/253 R X |
| 3,712,795 | 1/1973 | Hamshere et al. | 23/253 A X |
| 3,764,268 | 10/1973 | Kosowsky et a. | 23/253 R |

*Primary Examiner*—Robert M. Reese
*Attorney, Agent, or Firm*—Lane, Aitken, Dunner & Ziems

[57] ABSTRACT

A programmed fluid sampling and analysis apparatus and method includes apparatus for the programmer controlled sampling of a fluid stream in order to subject the fluid sample to an automated analysis of the ion or molecular concentrations of the chemicals of the sampled fluid. The sampled stream and appropriate reagents are impelled by a gas through the apparatus according to a program so that the sample fluid and reagents ultimately mix in a vessel wherein the mixtures are analyzed by a colorimeter or by specific element-ion sensitive probes connected to electronic amplifying and recording equipment. A programmed analysis of the sensor output is provided on a strip chart recorder. The apparatus includes a fluid sampling and transport device for delivering an aliquot of sampled fluid to a reaction chamber under the influence of a programmed pulse of compressed air. An aliquot of one or more reagents is similarly provided to the reaction chamber from a reagent sampling and transport device. The structures of the fluid sampling device, the reagent sampling device and the reaction chamber, in combination with the components of the system, permit automated analysis of a fluid stream. The details of the programmed circuit for performing the analysis are also disclosed.

25 Claims, 13 Drawing Figures

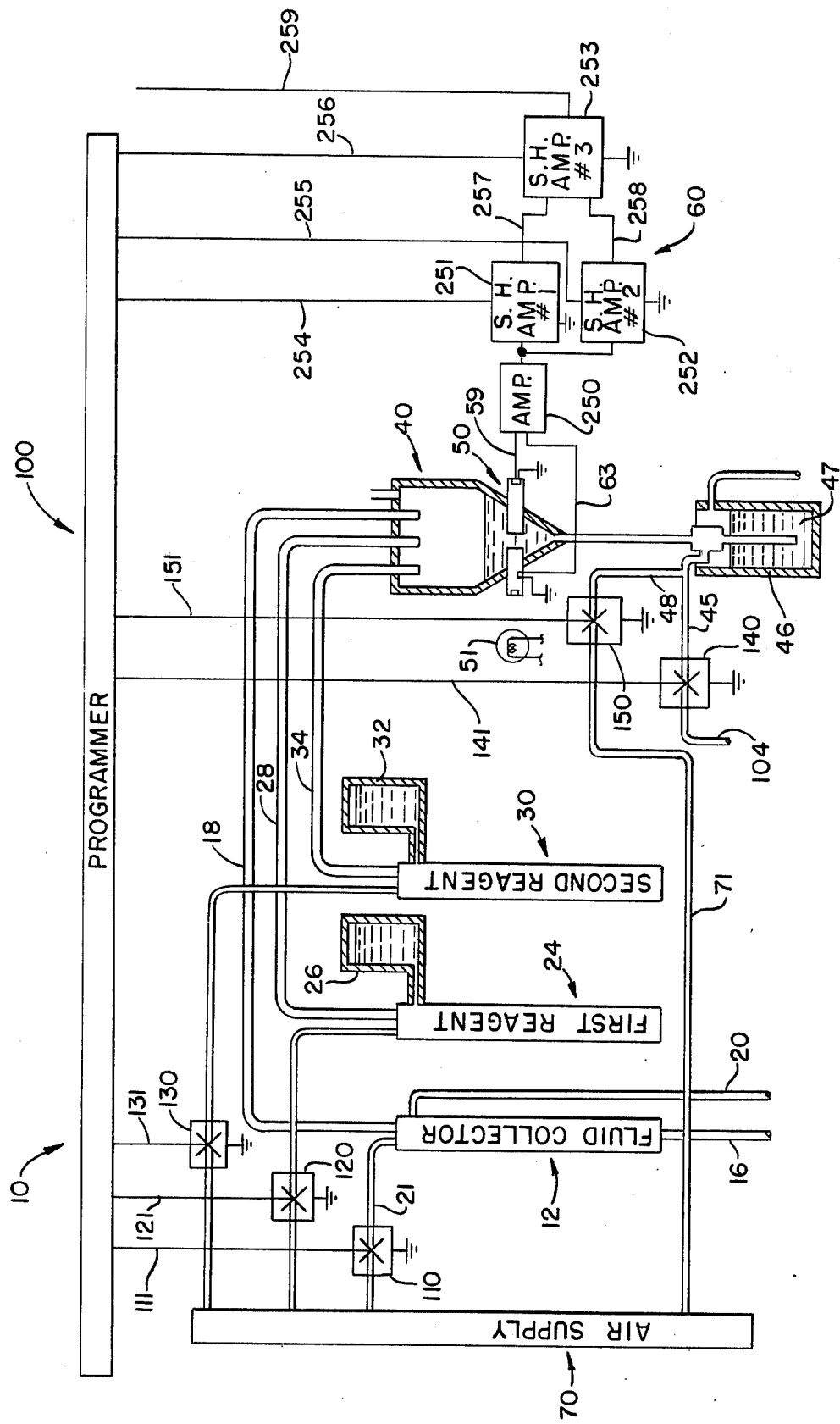
FIG. I.

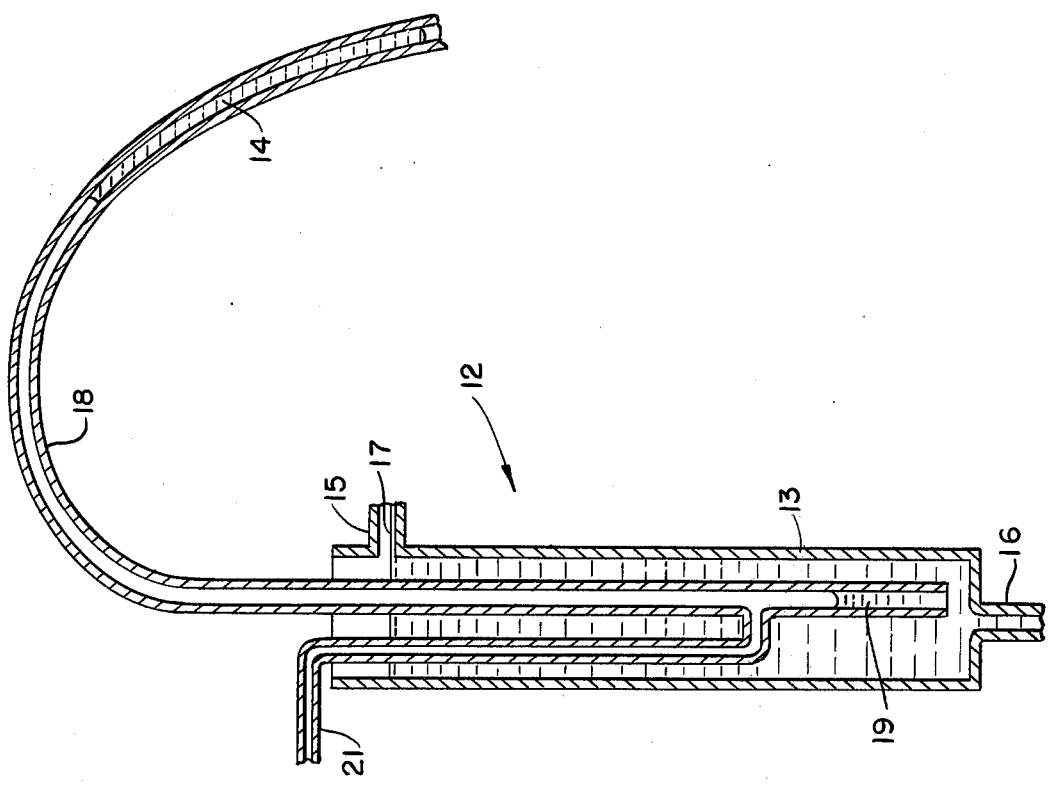
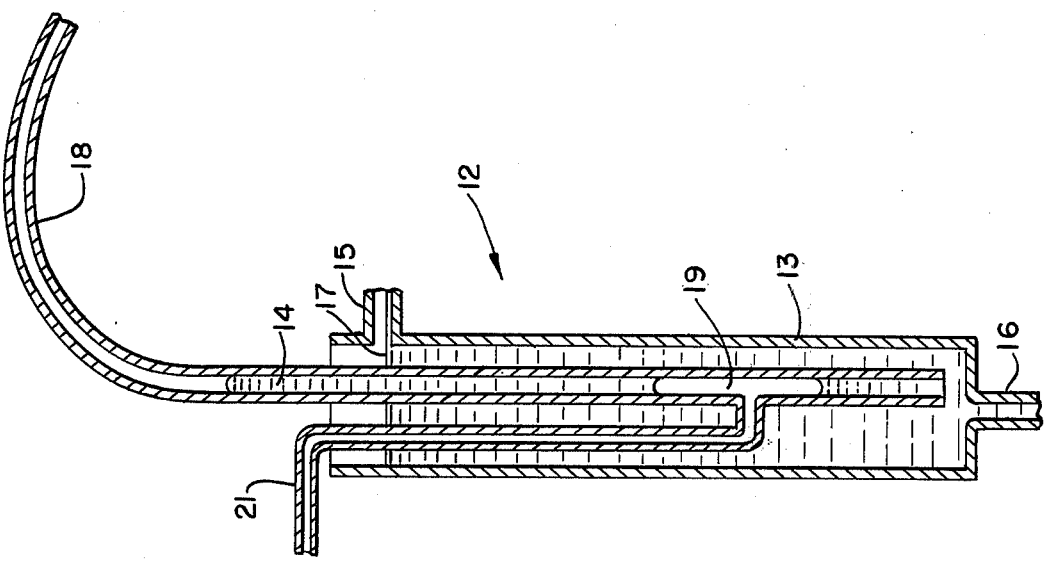
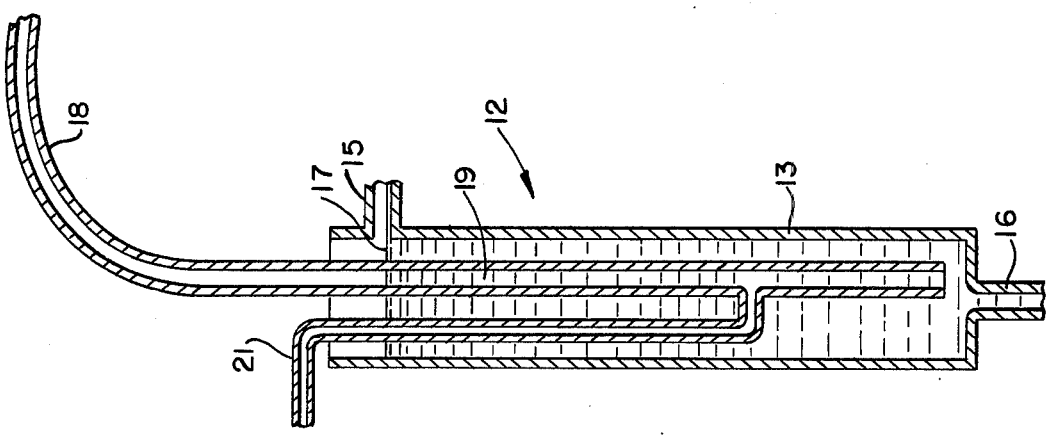

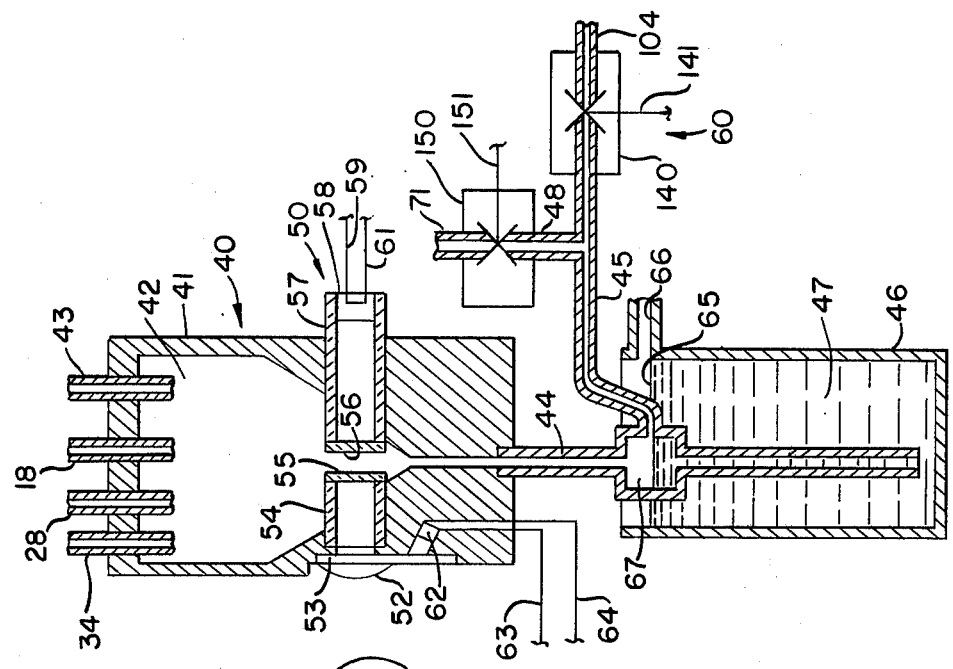
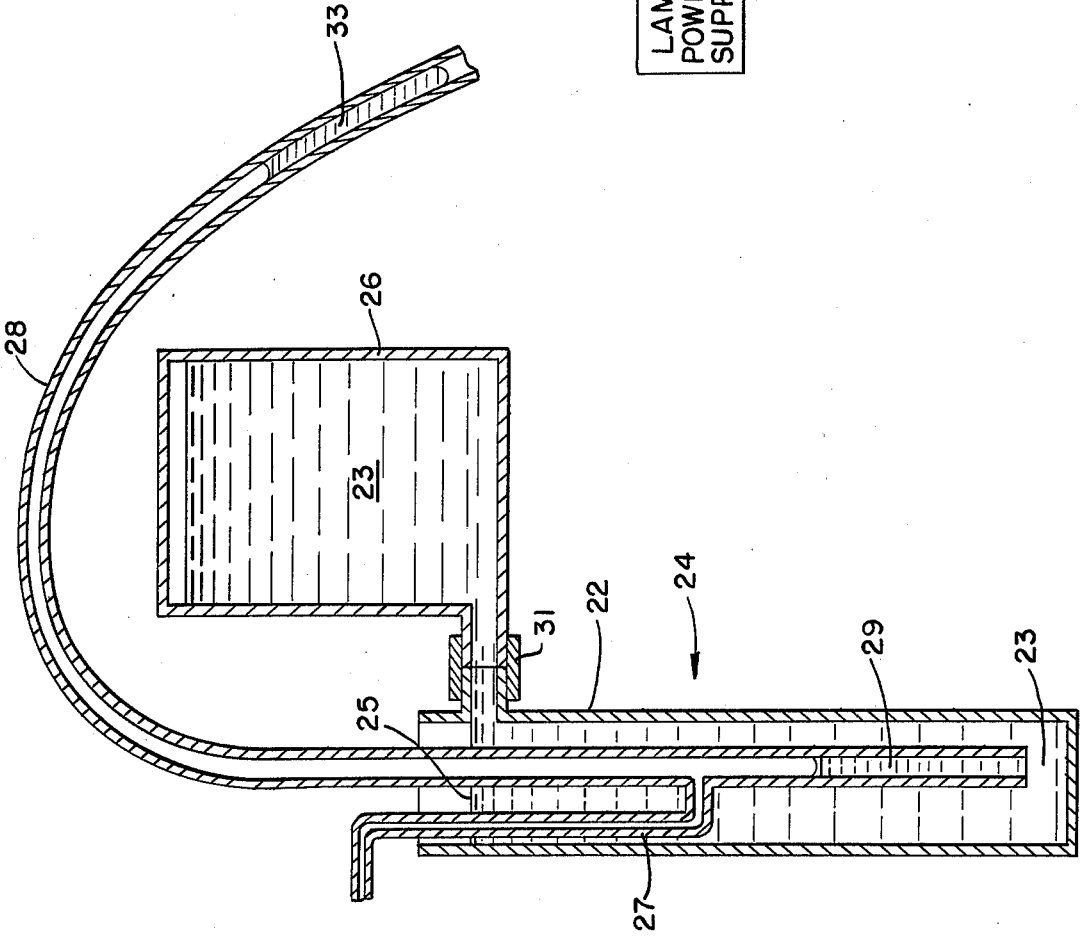

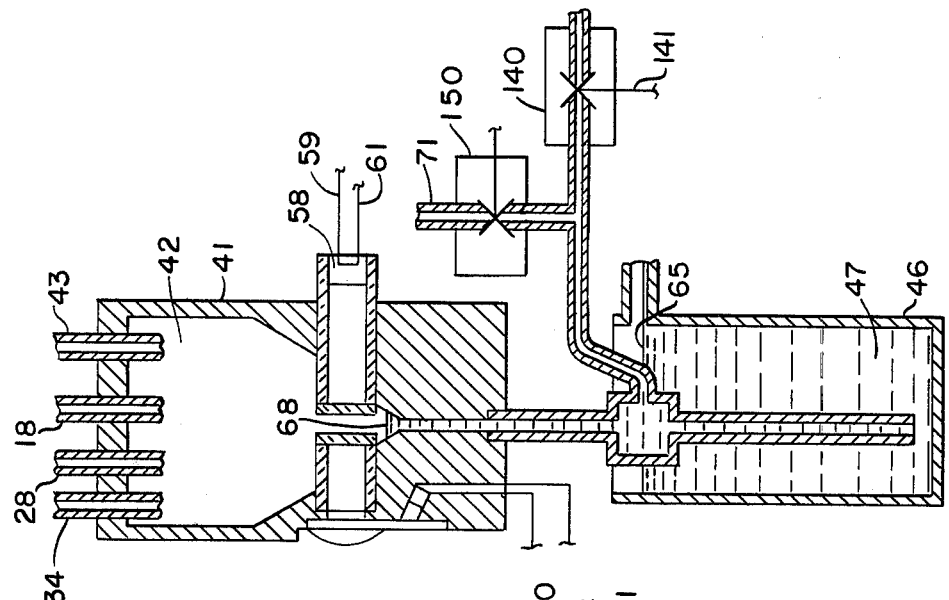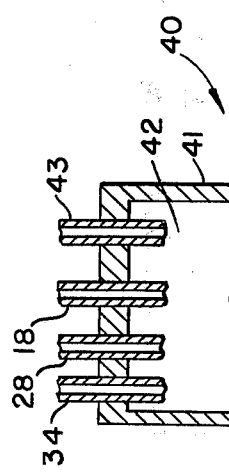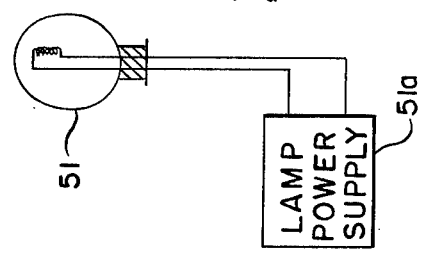

PROGRAMMED FLUID SAMPLING AND ANALYSIS APPARATUS

BACKGROUND OF THE INVENTION

This invention relates to a programmed fluid sampling and analysis apparatus and method. More particularly, this invention relates to such a method and apparatus which includes a programmer controlled sampling of a fluid stream to subject a sample of the fluid stream to an automated analysis of the ion concentrations of the chemicals of the sampled fluid. Still more particularly, this invention relates to novel fluid sampling and reagent sampling devices for transporting sampled fluid and reagents to a novel reaction chamber which devices and chamber cooperate with other components of the programmed apparatus to provide the above-mentioned programmed automated analysis.

It has long been an aim in the art to automate the analysis of fluid samples. Accordingly, a number of such automated instruments have been developed utilizing a wide variety of approaches. In the main, however, such devices have been deficient in automating, on a low maintenance basis, the transport of sampled fluids and reagents to a reaction zone.

For example, other apparatuses for sampling fluid streams which have been devised have usually employed either peristaltic pumps or liquid sampling valves with sliding surfaces in contact with each other, and have thus embodied certain disadvantages. In such devices of the type wherein discrete quantities of the fluid stream were sampled, the polished surfaces of the sampling valve generally used in such apparatuses were often scratched with suspended matter thus causing leaks and other maintenance difficulties.

Moreover, in prior art devices wherein a continuous process stream type sampling was used, the suspended matter in the process stream often became embedded in the walls of the peristaltic pump, eventually causing pump tubing failure. Furthermore, the suspended matter would accumulate in the tubing used for transporting the fluid from the pump to the reaction or holding chambers used in the analysis, eventually causing plugging of the interconnecting tubing. Still further, the pump tubing in the peristaltic pump in such apparatuses often fatigues and cracks after extended use, thus necessitating periodic replacement of the tubing.

Some of the above-mentioned objections were overcome by the automatic analyzer disclosed in U.S. Pat. No. 3,627,494, issued Dec. 14, 1971. However, in this device, suspended matter would accumulate in the colorimeter chamber and in the liquid types formed by the interconnecting tubing and passages and the colorimeter and reaction chamber could not be combined to decrease the response time of the instrument. This occurred because, in the described device, incoming air continued to flow into the reaction chamber which made impractical the reading of transmitted light changes as the air bubbles passed through the liquid and intercepted the light beam.

For further background for devices of the general type described, reference may be also made to U.S. Pat. No. 3,654,113 by the same inventor as in this invention. That disclosure is herein incorporated by reference.

It is, therefore, the broad subject of this invention to utilize a programmer in conjunction with a novel sampling device fo both the fluid stream and a reagent which includes no sliding or flexed surfaces and further utilizing measurement instrumentation for automatically programming an aliquot of a stream of fluid and several other reagent fluids through the system and for providing sequencing of the measurement instrumentation in a special discrete sampling technique.

It is another broad object of the invention to utilize such sampling devices which would prevent failure of the system due to precipitation of suspended solids into the interconnecting tubing and reaction containers.

It is still another object of this invention to provide a novel fluid sampling and transport device for use in an automated analyzer to provide a predetermined increment of sampled fluid without moving parts in contact with the liquid phases.

It is an additional object of this invention to provide such a novel sampling and transport device which does not require the flexing of passages or tubing.

It is a further object of this invention to provide a novel reagent sampling and transport device having the advantageous characteristics of the fluid sampling and transport device mentioned above.

It is still another object of this invention to provide a novel means for reacting and draining liquid mixtures for use in an automated analyzer.

It is still another object of this invention to provide such a novel means for reacting and draining liquid mixtures without moving valves or pumps or flexing surfaces in contact with the samples or reagents and particularly such a device wherein the combined liquid phase can be suspended in an elevated reaction chamber supported by air and liquid.

These and other objects of the invention will become apparent from a review of the accompanying written description of the invention taken in conjunction with the accompanying drawings.

BRIEF SUMMARY OF THE INVENTION

Directed to overcoming the problems of the prior art automated analyzers and achieving the aforementioned objects, the programmed fluid sampling and analysis apparatus according to the invention comprises a controlled source of compressed air communicating with a fluid sampling and transport device. The fluid sampling device comprises a vessel having an inlet for receiving the fluid to be sampled and an overflow outlet. A transport tube communicates with the fluid in the interior of the vessel and is connected at a predetermined position to an air supply tube to define a column of sampled fluid having a predetermined volume determined by the diameter of the tube and the difference between the location of surface of the fluid in the container and the location of the connection between the air supply tube and the transport tube. When a programmed pulse of air is made to the vessel through the air supply tube, an aliquot of sampled fluid is caused to be transported through the transport tube to a reaction chamber.

One or more reagent sampling and transport devices are also provided, each of which communicates with the controlled source of air and with the reaction chamber. The reagent sampling device includes a reservoir for the reagent to maintain the level of the reagent within the vessel of the device at a constant level. The reagent sampling device is otherwise quite similar to the fluid sampling device. Upon the admission of a programmed pulse of compressed air to the reagent sampling device, an aliquot of reagent is caused to be transported through a reagent transport tube to the reaction chamber.

The apparatus also includes a novel reaction chamber including a cavity for receiving and containing the fluid sample and reagents. By its novel construction, the admixture of sample and reagents is suspended in a reaction zone. The reaction chamber also includes sensor means, for example, the optical portion of colorimetric analyzer.

Means are also provided sensing the electrical signals from the light sensors. The sensing means include programmed electronic circuits influenced in operation by the programming means which also control the admission of air to the fluid sampling and reagent sampling devices mentioned above.

These and other components are discussed in detail later in this specification, as are the steps of the method according to the invention.

BRIEF DESCRIPTION OF THE DRAWINGS

In the drawings:

FIG. 1 is a composite electro-mechanical schematic diagram, partially in block form, of the component parts of the system according to the invention;

FIG. 2A is a detailed partial elevational view, partially in cross section, of a fluid sampling device of the invention showing an aliquot of process sample fluid about to be separated from the main body of the sample stream;

FIG. 2B is a view of the structure shown in FIG. 2A depicting the fluid sampling device wherein an aliquot of process sample fluid has been separated from the main body of the sample stream;

FIG. 2C is a detailed view of the structure shown in FIGS. 2A and 2B illustrating the fluid sampling device wherein the separated aliquot of process sample fluid is ready to be discharged into a reaction chamber;

FIG. 3C is a view of the structure shown in FIGS. 3A and 3B illustrating the fluid sampling device wherein an aliquot of reagent is ready to be discharged into the reaction chamber and a reagent reservoir is supplying reagent to the main body of the reagent as needed to keep the level constant as an aliquot of reagent is removed;

FIG. 4A is a detailed partial elevational view, partially in cross section, of the reaction chamber ready to accept aliquots of the sample and reagents and mix and react the aliquots prior to analysis by a colorimeter instrument built into the reaction chamber;

FIG. 4B is a view of the reaction chamber in FIG. 4A showing the reaction chamber containing a liquid mixture being discharged to waste;

FIG. 4C is a view of the reaction chamber in FIGS. 4A and 4B showing the liquid mixture almost totally drained from the reaction chamber;

FIG. 4D is an alternate embodiment of the reaction chamber showing a valve in the drain line;

DETAILED DESCRIPTION OF THE PREFERRED EMBODIMENTS

Figure 3A:
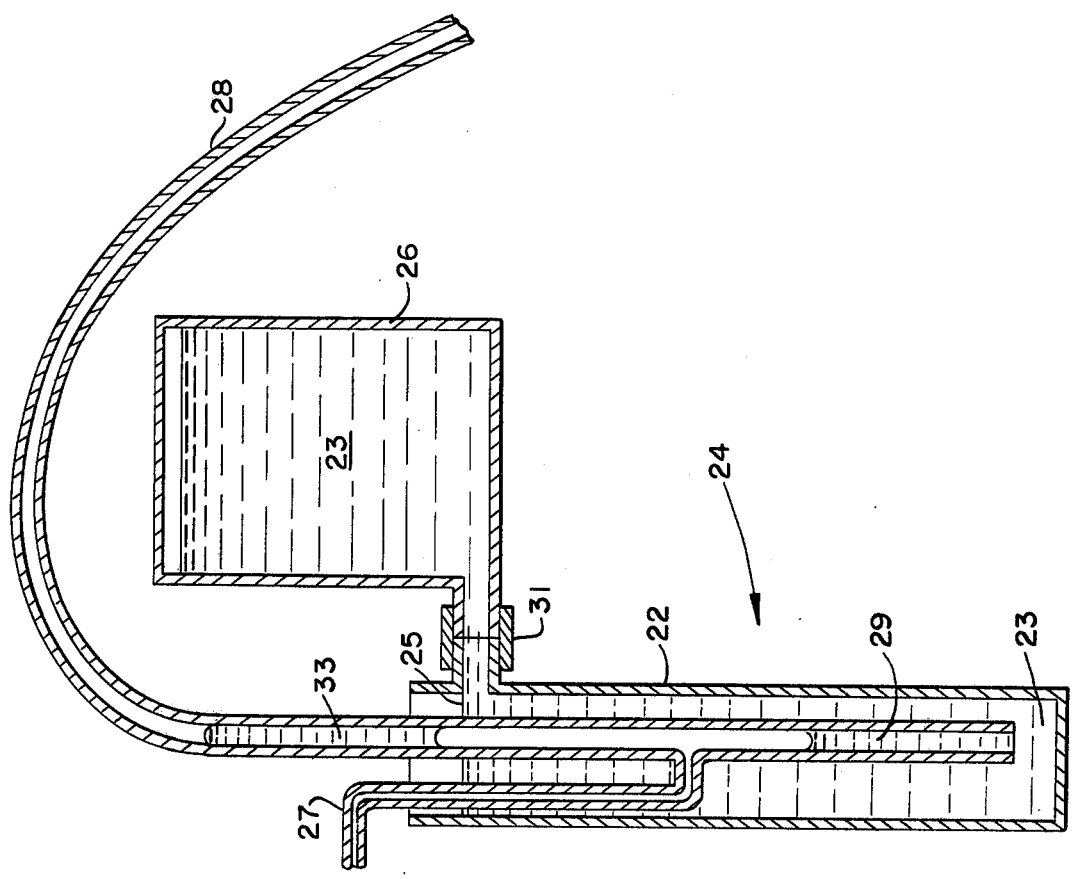
FIG. 3A is a detailed partial elevational view, partially in cross section, of a fluid sampling device of the invention showing an aliquot of reagent about to be separated from the main body of the reagent and a reagent reservoir for supplying reagent as needed to keep the liquid level constant as the aliquots of reagent are removed.

Structural Relationships of the System According to the Invention

FIGS. 1, 2A, 3A, 4A and 5 illustrate a combination of a group of components arranged in combination for producing a system for programmed fluid sampling and analysis. The combination includes an apparatus, designated generally by the reference numeral 10, which is programmer controlled for sampling a fluid stream in order to subject the fluid stream to analysis. The system according to the invention has the capability of transporting a predetermined portion of the fluid stream to be analyzed, and predetermined portions of preselected reagents and subsequently performing a colorimetric analysis. The system may be readily adapted to use other methods of analysis, such as selective ion electrodes.

The basic components of the system are described as follows with detailed discussion provided in connection with specific figures.

The apparatus 10 includes a first means, designated generally by the reference numeral 12 for collecting and transporting process fluid samples 14 to be analyzed from an input tube or source 16. The process fluid samples 14 are delivered by the collecting and transporting means 12 through tubing 18 to a reactor chamber, designated generally by the reference numeral 40. An overflow tube 20 is also provided for reasons to be discussed in connection with FIG. 2.

A second means, designated generally by the reference numeral 24, is included in the apparatus 10 for providing aliquots of a first reagent into the reaction chamber 40. A reservoir for supplying the first reagent is shown at 26. The reagent aliquots are delivered by means of tubing 28 to reactor chamber 40.

A third means, designated generally by the reference numeral 30, is included in the apparatus 10 for providing aliquots of a second reagent to the reaction chamber 40. A reservoir for supplying the second reagent is shown at 32. The second reagent is delivered to the reaction chamber 40 through tubing 34. Where necessary, or desired, additional reagent supplying means may be included to provide preselected reagents to the reaction chamber.

A fourth means, bearing the reference numeral 40, is included in the apparatus 10 for providing a reaction chamber for containing the reaction between the reagents from the second means 24 and the third means 30 and the process fluid aliquots from the fluid collecting and transporting means 12. The chamber 40 is also provided with the optical portion of a colorimetric analyzer instrument, designated by the reference numeral 50 and devices for draining spent reactants and process fluid.

A fifth means, designated generally by the reference numeral 60 are provided for reading the electrical signals from the light sensors of the colorimetric analyzer and providing an electrical voltage proportional to the chemical species being measured in the process fluid.

A sixth means, designated generally by the reference numeral 100, are provided for programming the electrical signals necessary to activate predetermined components of the system in a preselected fashion. Specifically, the programming means programs the operations of certain valves and electrical components of the apparatus 10 to produce the desired automated analysis of the fluid sample.

Finally, a seventh means for supplying compressed air is designated generally by the reference numeral 70. The details of the operation of the system will be described in detail below.

Structural Relationship of the Process Fluid Sampling Device

Referring specifically to FIGS. 2A, 2B and 2C, the structure and operation of the first means 12 for collecting and transporting fluid samples for analysis in the instrument system will be described. The collecting and transporting means 12 comprises a container vessel 13 having an inlet port or tube 16 and an overflow port or tube 15. The tube 18 is submerged below the liquid surface 17 of the liquid sample and the sample fluid fills the cavity 19 within the tube 18. The tube 21 is connected to the tube 18 at a predetermined depth below the liquid surface 17 to define a predetermined liquid column. The liquid column in the cavity 19 that is located above the junction of the tubes 21 and 18 is the aliquot that will be transferred from the first means 12 when a programmed short pulse of compressed air from the air supply 70 is admitted through the tube 21. The tube 21 is also connected to a solenoid valve 110 that permits air to flow into the tube 21 when an electrical signal is supplied by the programmer 100. When an electrical signal, such as a voltage pulse, is applied to the solenoid valve 110 by lead 111, an aliquot 14 of the sample fluid is separated from the main body of the fluid within the vessel 13 as shown in FIG. 2B. The aliquot 18 of sample fluid is caused to be transported through the tube 18 to the reaction chamber 40 by the pulse of air as shown in FIG. 2C.

The tubing diameter selected and the materials of construction chosen must be such as to permit the sample aliquot to be transported without slippage or back flow of some of the aliquot. In a practical embodiment, a tubing diameter of 0.25 in. worked satifactorily for water to produce a consistant collected sample of water on a weight (or volumetric) basis. For an air pulse of about 1.5 sec. duration at 5 psi inlet for a liquid column of 9.8 in. in a 0.25 in. diameter tube, the aliquot weight in grams varied only between 7.39 and 7.46. Thus, the disclosed structure worked satisfactorily to separate an aliquot of fluid from a body of the fluid and to transport the fluid through tubing to a desired location. Certain tubing materials in combination with certain liquid samples may not perform altogether satisfactorily if the surface tension of the fluid samples does not permit unhampered flow of fluid when the air pulse is applied.

It is a significant advantage of the fluid sampling device disclosed to avoid the need for pumps or metering valves that measure or meter fluid process streams, aliquots and reagents with considerable accuracy in analytical instrumentation such as that used for automated chemical analysis. Such a device as here disclosed avoids existing methods employing peristaltic pumps or sampling valves requiring considerable maintenance, due to fatigue, for peristaltic pump tubing, and valve surface wear on sliding contact for sampling valves. As is apparent, it is another considerable advantage of the invention to obviate the need for moving parts in contact with the liquid phases and to avoid requiring passages or tubing which must be flexed.

Structural Relationship of the First Reagent Sampling and Transport Device

Figure 3B:
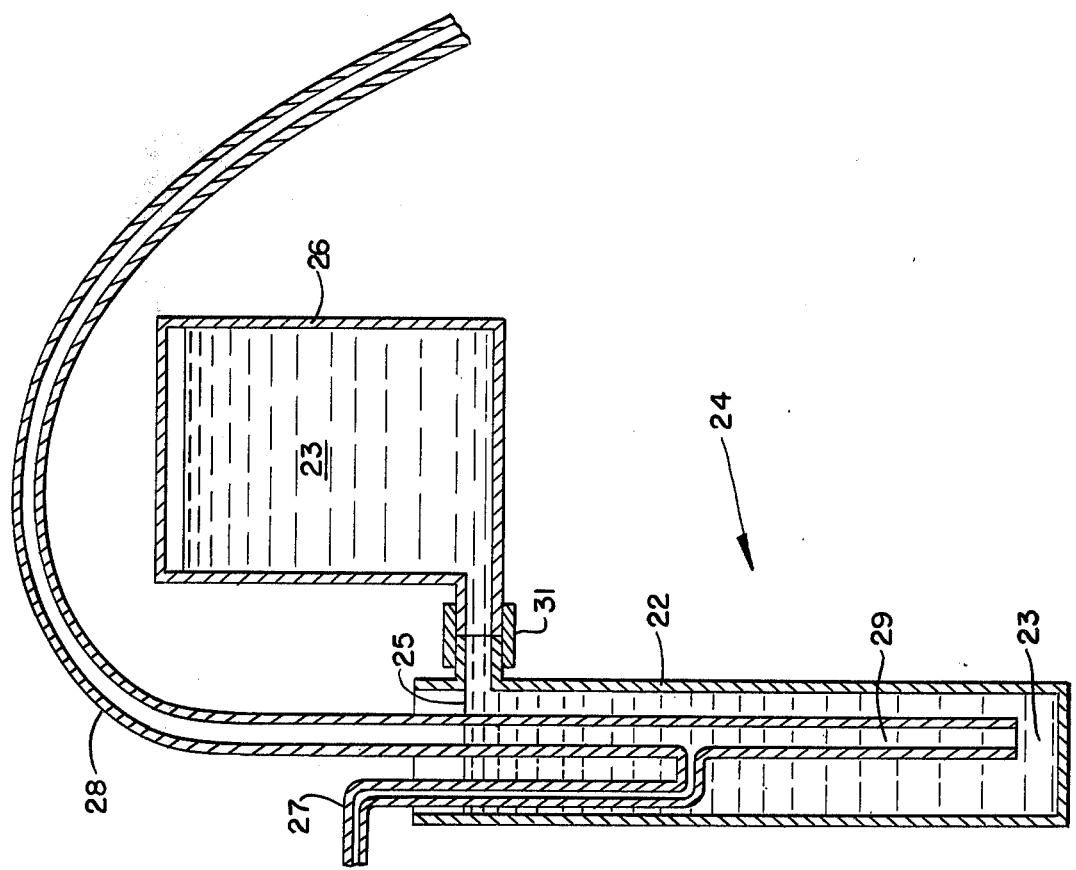
FIG. 3B is a view of the structure shown in FIG. 3A depicting the fluid sampling device wherein an aliquot has been separated from the main body of the reagent and the reagent reservoir is supplying reagent to the main body of the reagent as needed to keep the liquid level constant as an aliquot of reagent is removed.
Figure 5:
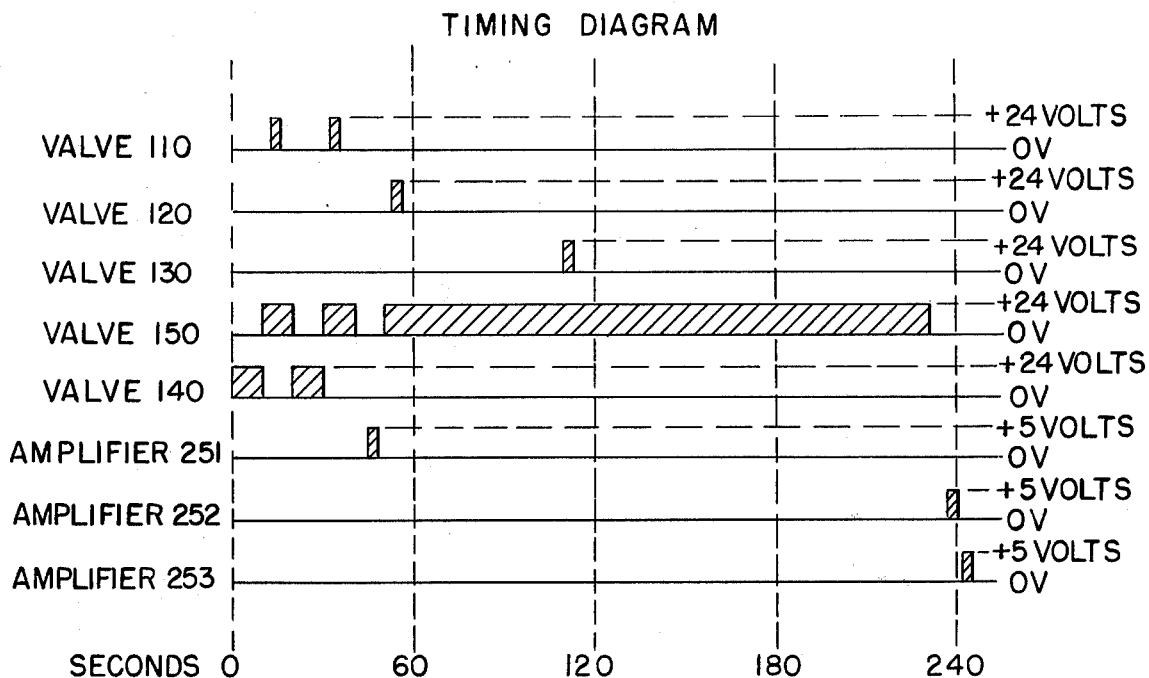
FIG. 5 is a timing diagram for the electronic timer used with the instrument system of the invention including a colorimeter sensor for the determination of phosphate in water.

Referring specifically to FIGS. 3A, 3B and 3C, the structure and operation of the second means 24 for providing an aliquot of a reagent into the reaction chamber 40 for use in the analysis provided by the instrument system is now discussed. The reagent sampling and transport means 24 includes a chamber 22 including a tube 28 submerged below the liquid surface 25 of the liquid reagent 23. A tube 27 is connected to the tube 28 at a predetermined point below the liquid surface 25 at one end to a solenoid valve 120 at the other end. The liquid column in the cavity 29 in the tube 28 that is located above the junction of tubes 27 and 28 is the aliquot that will be transferred from the second means 24 when a short pulse of compressed air is admitted through the tube 27. The same geometric and material of construction limitations discussed in connection with the fluid sampling and transport device of FIG. 2 apply to the reagent sampling and transport device of FIG. 3.

Air under pressure is supplied to the tube 27 whenever the programmer 100 supplies an electrical signal on the lead 121 to the solenoid valve 120. The reagent 23 in the reservoir 26 flows into the chamber 22 whenever the surface level 25 of the reagent drops and admits quantities of air into the reservoir 26.

The reservoir 26 is connected to the chamber 21 by a quick disconnect fitting 31 to facilitate filling the reservoir chamber 26 when the reagent 23 in the reservoir 26 is depleted.

When the solenoid valve 120 is activated with an electrical signal, such as a voltage pulse, from the programmer 100 via lead 121, an aliquot 33 of the reagent 23 is detached from the main body of the reagent 23 below the liquid surface 25, as is shown in FIG. 3B. The aliquot 33 of the reagent is transported to the reaction chamber 40 during the time the solenoid valve 120 is activated by the programmer 100, as shown in FIG. 3C.

The operation and construction of the reagent sampling and transport device shown in FIG. 3 is substantially like that shown in FIG. 2, except for the addition of the reagent reservoir 26 to dispense reagent therefrom.

It is an advantage in this device, as described earlier, to avoid moving surfaces or flexed tubes in contact with the liquid reagents. As a practical matter, the reagent reservoir can be made large enough to permit several days of operation of an automated analyzer without specific attention.

Structural Relationship of the Second Reagent Sample and Transport Device

The construction and operation of third means 30 (the second reagent sampling and transport device) is identical in construction and operation to the second means 24 shown and described in connection with FIGS. 3A, 3B, and 3C. The third means 30 is used to provide a second reagent and the second means is used to provide the first reagent as needed into the reaction chamber 40 in the manner previously described by a tube 34. A reagent dispensing reservoir is shown in FIG. 1 at numeral 32. The aliquot of the second reagent is caused to be transported to the reaction chamber 40 by the action of the valve 130 caused by a signal on a lead 131 from the programmer 100 to permit air from the air supply 80 to be admitted to the device 30.

Structural Relationship of the Reaction Chamber and Composition Sensor.

Referring to FIGS. 4A, 4B and 4C, the fourth means 40 (or reaction chamber means) consists of a chamber 41 defining a cavity 42 or reaction zone for admixing and containing the process sample from tube 18 and the reagents from tubes 28 and 34 and serving as a reactor site and a detector site. The aliquot of the process sample is introduced into the reaction cavity 42 through the tube 18 as described. The aliquot of the first reagent is introduced to the cavity 42 through the tube 28, while the aliquot of the second reagent is introduced into the reaction zone 42 through the tube 34. The tube 43 serves as a vent for excess gases that may be present or generated during normal operation. The chamber 41 includes a drain tube 44 that is submerged in the spent liquid 47.

The construction of the reaction chamber means 40, and particularly the selection of the material with certain surface properties and internal diameter of the tube 44 are determined by the fluid mixture in the cavity 42. Specifically, it is desired to suspend the liquid phase in the cavity 42 serving as an elevated reaction zone supported by a column of air and a column of liquid, as will be described.

A drain tube 44 having an internal diameter of 0.125 in. is satisfactory when made from a material such as that commercially available under the designation "Tygon", for example.

A glass tube having an internal diameter of 0.25 in. did not appear to work satisfactorily because water leaked into the line 44 and could not be supported above at the air-water interface as shown in FIG. 4B. Thus, the internal diameter of the tube 44 is chosen based on considerations of the viscosity and surface tension of the fluid to be supported.

The drain tube 44 has a gas-liquid disengagement zone 67 to which a tube 45 is attached at a port above the liquid surface 65. The tube 45 is attached to a tube 48 at a location that can be above the cavity 42 if needed to keep liquids from reaching the tube 48 when the liquid in the cavity 42 is draining. The tube 45 is attached to a solenoid 140 which is vented to the ambient air through a tube 104 when activated by an electrical signal, such as a voltage pulse on a lead 141, from the programmer 100. The tube 48 is connected to a solenoid 150 which is connected to a tube 71 from the air supply 70. Compressed air is supplied to the tube 48 when the solenoid valve 150 is activated by a voltage pulse on a lead 151 from the programmer 100.

The reaction chamber 42 serves as a housing for the colorimeter instrument which consists of a light source 51 activated by a source of power 51a, a light collimating lens 52, an interference filter 53, a light pipe 54 to which is attached a glass window 55, a second window 56, a second light pipe 57, a detector 58 whose one output lead 59 is connected to one input of a log ratio amplifier 250 and the other output 61 is connected to ground, and a second detector 62 whose one lead 63 is connected to the second input of the log ratio amplifier 250 and whose other lead 64 is connected to the signal ground.

Although a colorimeter is shown housed in the reaction chamber 41, other sensors such as selective ion electrodes and conductivity sensors could be housed in the reaction chamber 41 or in cooperation with the reaction chamber to perform other analyses. If other sensors or means of detection are used, other types of reagents unique to the needs of the chemistry involved in the analysis would be employed and the electronic circuitry selected on the basis of the transfer function of the sensor.

If desired, the solenoid valve 140 could be placed to intercept the tube 44 just below the cavity 67, while tubes 45 and 104 are eliminated. The chamber 46 could likewise be eliminated when solenoid 150 is moved to intercept the tube 44 as indicated.

Structural Relationship of the Electronic Amplifiers to the System

The inputs of the log ratio amplifiers are connected to the light detectors 58 and 62. The light detector 58 measures transmitted light passing through the sample liquid in the reactor chamber 42. The light detector 62 is used to compensate the output from the log ratio amplifier 250 for any variations in the intensity of the light source 51. The output of the log ratio amplifier 250 is connected to the inputs of the sample and hold amplifiers 251 and 252, the outputs of which are connected to the difference and sample and hold amplifier 253. The sample and hold amplifiers 251, 252, and 253 are triggered by signals on leads 254, 255 and 256 respectively to update readings from the colorimeter light detectors 58 and 62 on command from the programmer 100 at intervals specified in the timing diagram in FIG. 5.

Structural Relationship of the Programmer to the System

Figure 6:
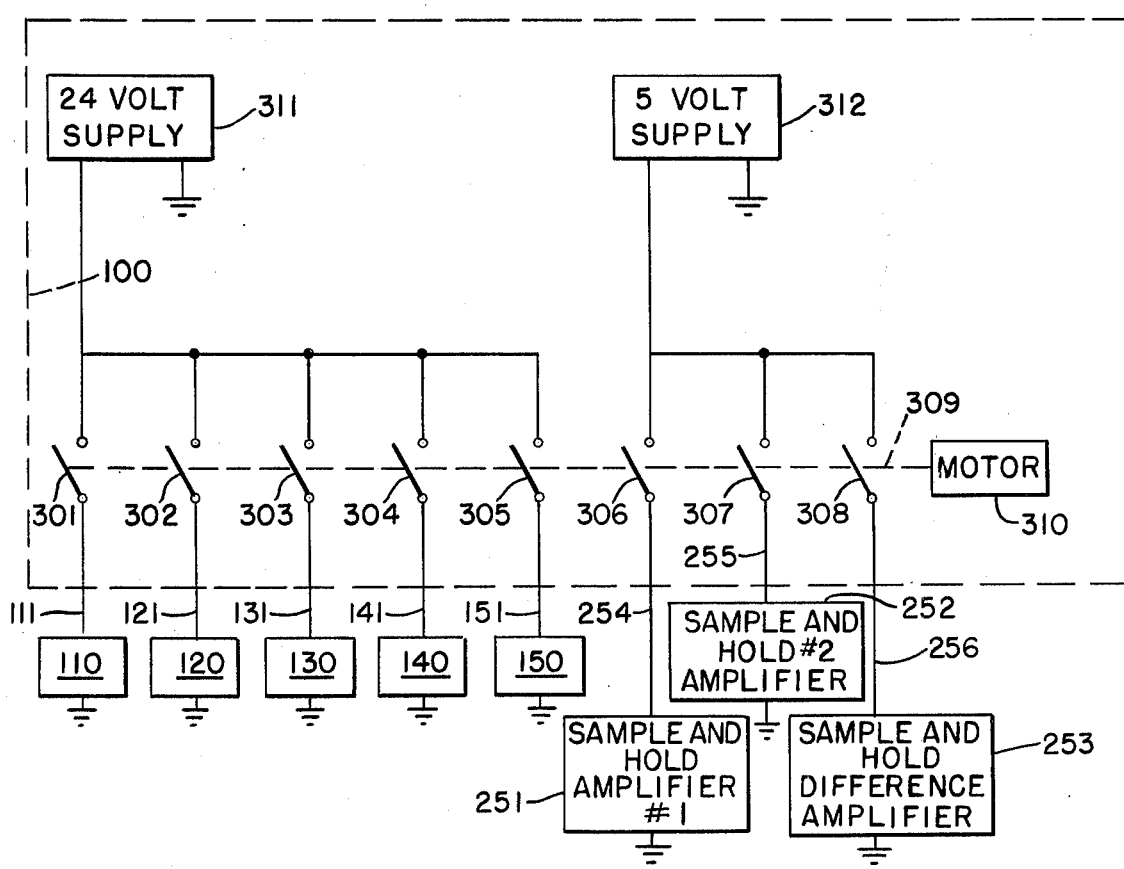
FIG. 6 is a circuit diagram for the system of the invention for programming the operation of the valves and amplifiers according to the timing diagram of FIG. 5.

Referring to FIG. 6, the programmer 100 consists of a cycling timer [designated generally by the reference numeral 300] (Cramer Company Model No. 540-3M) containing eight microswitches 301–308 actuated by eight individual cams (not shown) mounted on a continuously rotating shaft 309 driven by an electric motor 310 and connected to 24 volt and 5 volt power supplies 311 and 312. The programmer supplies voltage pulses to energize the solenoid valves and activate the sample and hold amplifiers in the sequence shown in FIG. 5, which for purposes of illustration was determined specifically for the determination of phosphates in water by means of colorimetric procedures carried out in the instrument system. A programmer constructed of electronic timers, type 555, and suitable driver circuits, would also operate satisfactorily, as would more complex electronic circuitry utilizing microcircuiting and the like.

Structural Relationship of the Air Supply to the System

The air supply 70 can be derived from an air compressor or bottled compressed air. The air from the air supply can reach the selected points in the instrument system through the solenoid valves that are actuated by the programmer according to the sequence in the timing diagram in FIG. 5.

Operational Relationship within the Fluid Sampling and Transport Device

Referring to FIGS. 2A, 2B, and 2C and occassionally to the other figures, process sample water continuously flows through inlet 16 into the container vessel 13, and out the overflow 15 so that a column of process sample fills the cavity 19. On command from the programmer 100, a pulse of compressed air is injected through the tube 21 and an aliquot of liquid 14 is detached from the main body of liquid below the liquid surface 17 as the compressed air enters the cavity 19. The aliquoit of fluid sample is transported to the reactor cavity 42 as the compressed air continues to enter the cavity 17. An indicated, the size of the aliquot 14 is determined by the distance between the surface 17 and the point at which tube 21 joins the tube 18 and the internal cross sectional area of th tube 18.

The air pulse must be discontinued after the aliquot is ejected from the tube 18; otherwise, quantities of liquid slugs will rise past the junction of the tube 21 and the tube 18 and be likewise transported out of the tube 21 in unpredictable volumes.

Operational Relationship within the First Reagent Sampling and Transport Device Referring to FIGS. 3A, 3B and 3C and occasionally to the other figures, the reagent liquid 23 in the reservoir 26 is in open communication with the chamber 22 and always flows into the chamber 22 whenever the liquid surface level 25 drops and admits quantities of air into the reservoir 26. A pulse of compressed air is injected through the tube 27 and an aliquot 33 of the reagent 23 is detected from the main body of liquid below the surface 25. As the compressed air pulse continues to enter the tube 27 the aliquot 33 is transported to the reactor cavity 42. The size of the aliquot 33 is determined by the distance between the surface 25 and the point at which the tube 27 joins the tube 28 and the internal cross sectional area of the tube 28. The air pulse must be disconnected after the aliquot is ejected from the tube 28; otherwise, quantities of liquid slugs will rise past junction of tube 27 and 28, and be likewise transported out of tube 28 in very unpredictable volumes.

Operational Relationship within the Second Reagent Sampling and Transport Device The second reagent sampling and transport device 30 is identical to the first reagent sampling and transport device 20 except for the size of the aliquot of the second reagent that is separated and transported to the reaction chamber 42. The size of that aliquot is determined as previously indicated in connection with the requirements of the chemistry of the system.

Operational Relationship within the Reaction Chamber and Composition Sensor

Referring specifically to FIGS. 4A, 4B, and 4C and occasionally to the other figures, the solenoid 150 is opened on command from the programmer 100 and compressed air flows through the tube 48 into the tube 45 and thus into tube 44 whereupon the air enters the cavity 42 and is vented through the passage 43. As an aliquot 14 enters through the entry tube 18 into cavity 42, it remains suspended in the cavity 42 as long as the solenoid valve 141 remains closed. After the solenoid valve 150 is turned off by the programmer, the liquid immediately below the surface 68 and above the opening 69 is supported by a column of water between the surface 65 and the surface 73, the pressure is transmitted by the static column of air 72 between the liquid at the opening 69 at the liquid surface 73, and the surface tension of the liquid at the opening 69 prevents the liquid from entering the opening so long as the static column of air is maintained at the required pressure under quiescent conditions, i.e., where the liquid phase is suspended in the manner described or at least a portion of which is maintained in the optical path of the colormeter to permit analysis. The first and second reagents are added through inlet tubes 28 and 34 respectively while the liquid above the opening 69 is supported by the water column in the container 46. The aliquots added to cavity 42 are agitated and mixed during the reaction within the cavity 42 when the valve 150 is opened by a voltage pulse supplied by the programmer 100 and compressed air is admitted through the tube 45 and flows into the reaction chamber 42 through the tube 44.

The colorimeter consisting of light source 51, collimating lens 52, optical light filter 53, light tube 54, window 55, window 56, light tube 57, detector 58, detector 61 used for compensating for variations in light intensity and electronic amplifiers 250, 251, 252, 253, is used to measure the transmitted light passing through the liquid between the light windows 55 and 56 both before and after the reagents are added to the process sample aliquot and convert these transmitted light readings into a log ratio voltage output signal which is a linear function of the concentration of the chemical species that absorbs light in the wave length interval defined by the light filter 53.

When the process stream aliquot 14 enters the cavity 42, the amplifier 251 is activated to read and hold the output signal from the log ratio amplifier 250 after the reagents are added and allowed to react. The amplifier 252 is activated by the programmer 100 to read and hold the output from the log ratio amplifier 250 after which the difference sample and hold amplifier 253 is activated by the programmer 100 to read the difference in output signals from the amplifiers 251 and 252 and update and hold this difference signal until the next command from the programmer to amplifier 253. This difference signal is the log of the ratio of the transmitted light signal before addition of reagents to the transmitted light signal after the addition of reagents. This difference signal is commonly referred to as absorbance in the field of analytical chemistry where optical instruments are employed. Absorbance is usually a linear function of concentration of the chemical species being analyzed. It should be noted that the absorption of light by any suspended matter is compensated for because transmitted light readings are made before and after the reagents are added and the error contributions due to suspended matter are cancelled when the absorbence is thus computed electronically.

Operational Relationship within the Instrument System

For purposes of illustrating a specific example, the instrument system is now defined for the analysis of phosphate in waste water. The programmer 100 was arranged to deliver the voltage pules specified in the timing diagram in FIG. 5. The following sequence of events occurs during a typical 250 second time cycle. The valve 140 is activated for 10 seconds to drain any liquid in the cavity 42. The valve 150 is activated for 10 seconds while valve 110 is activated 2 seconds later to transport an aliquot 14 of the process sample to the cavity 42 to flush residual liquid droplets remaining after the previous analysis cycle. Valve 140 is again activated to permit liquids in cavity 42 to drain into the container 46. The valve 150 is then again activated to bring compressed air into the cavity 42 while a process stream aliquot is transported from the first means 12 to the reactor cavity by activating the valve 110 for about 2 seconds. Next, compressed air flow to the cavity 42 is stopped when valve 150 is deactivated and amplifier 251 is activated to read and hold the transmitted light signal from the log amplifier 250. Next, the first reagent is added by activating the solenoid valve 120 at about the same time valve 150 is activated to supply compressed air to the cavity 42 to agitate the liquids in the cavity 42. After about 60 seconds, valve 130 is activated and the second reagent is added for the second stage of the reaction to proceed for an interval of about 120 seconds after which valve 150 is deactivated to stop the air flow and allow any air bubbles to leave the liquid phase in the cavity 42. The amplifier 252 is then activated shortly before 240 seconds to read and hold the transmitted light signal from the amplifier 250 and immediately thereafter, the amplifier 253 is activated to read and hold the difference between the signals from amplifiers 251 and 252 and produce an output signal that is a linear function of the concentration chemical species (phosphate ion) being analyzed. The specific chemistry of the reaction, the precise reagents and nature of the accompanying reactions are within the skill of the art.

It should be pointed out that suspended solids present in the process sample aliquot do not accumulate because liquids being transported in the tubing 18, 28, and 34 move at a high velocity and liquids draining through tube 44 out of cavity 42 are moved by gravity force without encountering any obstacles such as liquid traps.

Thus, a programmed automated analytical instrument has been described.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. A controlled apparatus for incrementally sampling a fluid in order to subject a discrete portion of the sampled fluid to analysis and having the capability of transporting at least said discrete portion of the sampled fluid free from contact with mechanical pumps by propulsion caused by gas, said apparatus comprising the combination of:

gas supply means for supplying gas to propel said discrete fluid portion and at least a reagent in said apparatus in a predetermined sequence upon command;

fluid collecting and transporting means for both discretely collecting at least a portion of said fluid at a first location and transporting a predetermined portion of the sampled fluid to another location in response to a gas from said gas supply means;

reagent collecting and transporting means for both collecting a known aliquot of at least one reagent related to said predetermined portion of said sampled fluid and transporting said known aliquot to said another location in response to a gas from said gas supply means;

reactor means for providing a reaction zone at said another location for receiving and reacting said sampled fluid portion and said reagent portion, said reactor means including means for draining the reactor means of spent solution of said sampled fluid and said reagent in response to gas from said gas supply means;

means for programming the transportation of the predetermined portion of the sampled stream from said fluid collecting and transport means and said reagent portion from said reagent collecting and transport means by programming the supply of a gas to said fluid collecting and transport means and said reagent collecting and transport means;

means for analyzing the reaction products in said reaction zone to determine the ion concentration of predetermined chemicals of said fluid; said draining means being in communication with said gas supply means and said reaction zone for draining said reaction means from said reaction zone after analysis of said reaction products is complete in response to a gas from said gas supply means controlled by said programming means; and means in circuit with said analyzing means and said programming means for providing a signal represenative of said analysis.

2. The apparatus as set forth in claim 1 wherein said reagent collecting and transport means includes means for collecting a known aliquot of a second reagent and transporting said known aliquot of said reagent also related to said predetermined portion of said sampled fluid to said another location.

3. The apparatus as set forth in claim 1 wherein said gas supply means is an air supply means for supplying air in a predetermined sequence to said fluid collecting and transport means and said reagent collecting and transport means, said air supply means being controlled by said programming means to cause said predetermined portion of said sampled fluid and said known aliquot of said reagent to be transported respectively to said reaction zone.

4. The apparatus as set forth in claim 1 wherein said circuit means include readout means for measuring a difference in absorbence as the ratio of a signal representative of transmitted light through said sampled fluid prior to the addition of a reagent to the signal after the addition of at least one reagent.

5. The apparatus as set forth in claim 1 wherein said fluid collecting and transport means comprises:

means for selecting and containing said predetermined portion of the sampled fluid, said selecting and containing means being in communication with said programmed gas supply means so that said known aliquot is caused to be transported from said selecting and containing means by said gas supply means when gas is supplied thereto.

6. The apparatus as set forth in claim 5 wherein said containing means include a sample tube immersed in said fluid for receiving a sample of said fluid therein; a gas supply tube connected to said sample tube at a predetermined location intermediate the length thereof, and means for maintaining the height of said fluid sample at a constant level, a difference in location between the constant level of said fluid sample and said predetermined location defining said sampled fluid portion within said sample tube, said sampled fluid portion being transported to said reaction zone upon admission of a gas to said sample tube through said gas supply tube.

7. The apparatus as set forth in claim 6 wherein said fluid collecting and transporting means include a vessel for containing said fluid, said sample tube being immersed within said vessel and said constant level maintaining means includes an overflow port in said vessel.

8. The apparatus as set forth in claim 6 wherein said programming means include valve means in circuit with said gas supply means and said gas supply tube, and means for selectively actuating said valve means to cause a gas to be supplied to said gas supply tube.

9. The apparatus as set forth in claim 1 wherein said reagent collecting and transport means comprises:
means for selecting and containing said known aliquot of a reagent, said selecting and containing means being in communications with said programmed gas supply means so that said known aliquot of said reagent is caused to be transported from said selecting and containing means by said gas supply means when a gas is supplied thereto.

10. The apparatus as set forth in claim 9 wherein said selecting and containing means include a sample tube immersed in said reagent for receiving said reagent therein, a gas supply tube connected to said reagent tube at a predetermined location, and means for maintaining the height of said reagent at a constant level, a difference in location between the constant level of said reagent and said predetermined location defining said known aliquot of said reagent within said sample tube, said predetermined portion being transported to said reaction zone upon admission of gas to said sample tube through said gas supply tube.

11. The apparatus as set forth in claim 10 wherein said reagent collecting and transport means include a vessel for containing said sample, said containing tube being immersed within said vessel and said constant level maintaining means include a reservoir for said reagent connected to said vessel at about the height of said constant level so that when the reagent in the vessel drops below said height, reagent from said reservoir restores the reagent to said height.

12. The apparatus as set forth in claim 10 wherein said programming means include valve means in circuit with said gas supply means and said gas supply tube and means for selectively actuating said valve means to cause gas to be supplied to said gas supply tube.

13. The apparatus as set forth in claim 1 wherein said reactor means include first containing means for receiving said sampled fluid and said reagent to provide a reaction zone therefore; second containing means for receiving the reaction products of said fluid and said reagent; said draining means connecting said first and said second containing means and structurally adapted to prevent in cooperation with said gas supply means and said programming means the passage of reaction products therethrough under quiescent conditions.

14. The apparatus as set forth in claim 13 wherein said draining means include a disengagement zone, said gas supply means communicating with said gas disengagement zone and said programmed gas supply means for supplying a gas to said reactor means in a predetermined sequence.

15. The apparatus as set forth in claim 14 wherein said analyzing means include a colorimeter, the optical portion of which is in optical communication with the reaction products in said first containing means.

16. The apparatus as set forth in claim 14 wherein said reactor means is structured so that said fluid and said reagent remain suspended in said reaction zone when said gas supply means is off.

17. The apparatus as set forth in claim 14 wherein said gas supply means communicating with said disengagement zone include a first tube, the passage of gas through which is controlled by first valve means in said programming means, a second tube communicating with said first tube and controlled by second valve means in said programming means, the reaction products remaining in said reaction zone when said first valve means and said second valve means are closed.

18. The apparatus as set forth in claim 14 wherein said gas supply means communicating with said disengagement zone include a first tube, the passage of gas through which is controlled by first valve means in said programming means, and second valve means in said programming means in communication with said draining means, the reaction products remaining in said reaction zone when said first valve means and said second valve means are closed.

19. A liquid dispensing apparatus comprising:
means for selecting and containing a predetermined portion of a sampled liquid, said selecting and containing means being in communication with programmed gas supply means so that said predetermined portion of the sampled liquid is caused to be transported from said selecting and containing means by said gas supply when gas is supplied thereto, said selecting and containing means including a sample tube immersed in said liquid for receiving said sample therein, a gas supply tube connected to said sample tube at a predetermined location intermediate said sample tube, and means for maintaining the height of said sample at a constant level, a difference between the location of said constant level of said fluid and said predetermined location defining said predetermined portion of said collected fluid within said sample tube, said predetermined portion being transported from said sample tube upon admission of gas to said sample tube through said gas supply tube.

20. The apparatus as set forth in claim 19 wherein said liquid dispensing apparatus includes a vessel for containing said sample, said sample tube being immersed within said vessel and said constant level maintaining means include an overflow port in said vessel.

21. The apparatus as set forth in claim 20 wherein said constant level maintaining means include reservoir means for storing said liquid, said reservoir means communicating with said vessel to maintain the liquid level constant within said vessel.

22. In an apparatus for reacting a plurality of fluids, a reactor means including first containing means for receiving at least a first fluid and a second fluid to provide a reaction zone therefor; second containing means for receiving the reaction products of said first and second fluids; drain means connecting said first and said second containing means and structurally adapted to prevent, in cooperation with programmed gas supply, the passage of reaction products therethrough under quiescent conditions, said drain means including a disengagement zone, said gas supply means communicating with said disengagement zone; said programmed air supply means supplying air to said reactor means in a predetermined sequence to prevent reaction products from draining through said drain means when said gas supply means is in a first condition and causing said draining in said second condition.

23. The apparatus as set forth in claim 22 wherein said reactor means are structured so that said first and second fluids remain suspended in said reaction zone when said gas supply means is in said first condition; said suspension being maintained by a column of fluid and gas in said drain means and said second containing means.

24. The apparatus as set forth in claim 23 wherein said gas supply means communicating with said disengagement zone includes a first tube, the passage of air through which is controlled by first valve means operated by programming means, a second tube communicating with said first tube and controlled by second valve means operated by said programming means, the reaction products remaining in said reaction zone when said first valve means and said second valve means are closed, and draining therefrom when one of said valve means is open.

25. The apparatus as set forth in claim 23 wherein said gas supply means communicating with said disengagement zone includes a first tube, the passage of gas through which is controlled by first and second valve means operated by programming means, in communication with said drain means such that substantially no draining occurs when said first valve means and said second valve means are closed, and draining occurs when one of said valve means is open.

* * * * *

UNITED STATES PATENT OFFICE
CERTIFICATE OF CORRECTION

Patent No. 4,025,311   Dated May 24, 1977

Inventor(s)   Julius H. Bochinski

It is certified that error appears in the above-identified patent and that said Letters Patent are hereby corrected as shown below:

Column 1, line 52, "types" should read -- traps --;

Column 1, line 66, "subject" should read -- object --;

Column 1, line 68, "fo" should read -- for --;

Column 2, line 56, "made" should read -- admitted --;

Column 3, line 10, -- for -- should be inserted before "sensing";

Column 7, line 49, "port" should read -- point --;

Column 7, line 66, -- glass -- should be inserted after "second";

Column 8, line 57, "555" should not be in bold type;

Column 8, line 59, "microcircuiting" should read -- microcircuits --;

Column 9, line 14, "An" should read -- As --;

Column 9, line 18, "th" should read -- the --;

Column 9, line 34, "detected" should read -- detached --

Column 10, line 12, "colormeter" should read -- colorimeter --;

Column 10, line 64, "pules" should read -- pulses --;

UNITED STATES PATENT OFFICE
CERTIFICATE OF CORRECTION

Patent No. 4,025,311                    Dated May 24, 1977

Inventor(s)  Julius H. Bochinski

It is certified that error appears in the above-identified patent and that said Letters Patent are hereby corrected as shown below:

(Cont.)

Column 12, line 32, "presenative" should read
  -- presentative --;

Column 12, line 36, -- second -- should be inserted before
  "reagent";

Column 13, line 9, "transporting" should read -- transport --;

Column 13, line 22, "communications" should read
  -- communication --;

Column 13, line 56, "therefore" should read -- therefor --;

Column 14, line 66, -- means -- should be inserted after
  "supply" but before the comma [,];

Column 15, line 6, "said" should read -- a --.

Signed and Sealed this thirtieth Day of August 1977

[SEAL]

Attest:

RUTH C. MASON
Attesting Officer

C. MARSHALL DANN
Commissioner of Patents and Trademarks